United States Patent [19]

Dougherty

[11] Patent Number: 4,515,295
[45] Date of Patent: May 7, 1985

[54] EYE DROPPER WITH LIGHT SOURCE

[75] Inventor: Delford O. Dougherty, Shaker Heights, Ohio

[73] Assignee: St. Luke's Hospital, Cleveland, Ohio

[21] Appl. No.: 529,357

[22] Filed: Sep. 6, 1983

[51] Int. Cl.³ .............................................. A61M 1/00
[52] U.S. Cl. .................................. 222/113; 222/420; 362/96; 362/101; 362/191; 604/300
[58] Field of Search ............... 222/113, 192, 420, 215; 604/294, 295, 300, 302, 20; 362/96, 198, 101, 190, 191, 200; 128/23

[56] References Cited

U.S. PATENT DOCUMENTS

| | | | |
|---|---|---|---|
| 1,101,327 | 6/1914 | Philbrick | 362/191 X |
| 1,181,261 | 5/1916 | Schmidt | 362/96 |
| 1,702,967 | 2/1929 | Hays | 362/191 X |
| 2,307,745 | 1/1943 | Lutz et al. | 362/191 X |
| 2,382,771 | 8/1945 | Bowers | 604/300 |
| 2,500,639 | 3/1950 | Lermer | 222/215 |
| 2,547,450 | 4/1951 | DuPont | 222/113 |
| 2,577,857 | 12/1951 | Parisotto | 222/113 |
| 3,598,121 | 8/1971 | Lellicoff | 604/302 |
| 4,215,389 | 7/1980 | Colangelo | 362/200 X |

FOREIGN PATENT DOCUMENTS

| | | | |
|---|---|---|---|
| 293065 | 12/1953 | Switzerland | 222/113 |
| 564484 | 7/1975 | Switzerland | 222/113 |

*Primary Examiner*—Joseph J. Rolla
*Assistant Examiner*—Frederick R. Handren
*Attorney, Agent, or Firm*—Body, Vickers & Daniels

[57] ABSTRACT

A device for illuminating an area immediate to the dispensing orifice of a compressible eye drop dispenser. A miniature light source is held in a fixed, predetermined relationship with respect to the dispenser and provides a collimated beam of light which projects onto, and illuminates, the dispensing orifice.

5 Claims, 5 Drawing Figures

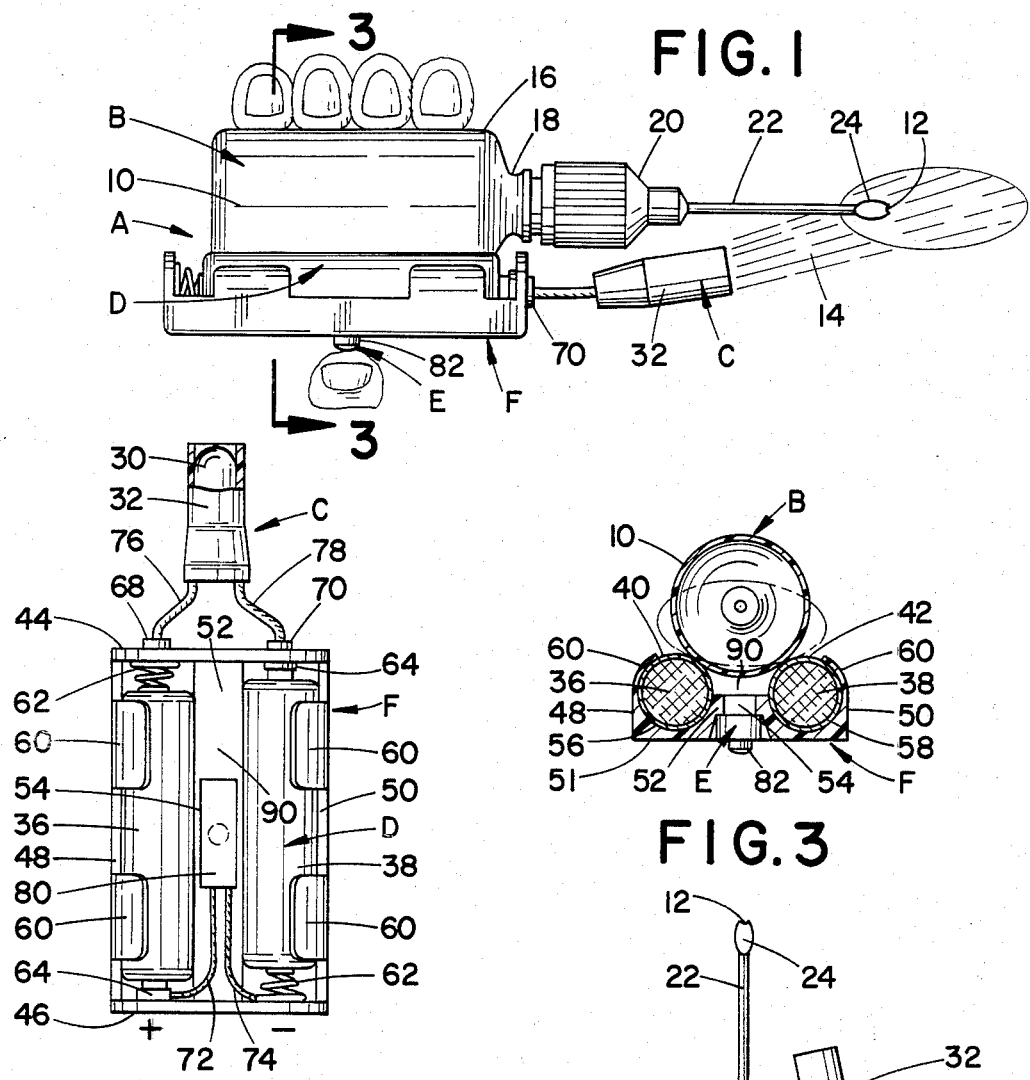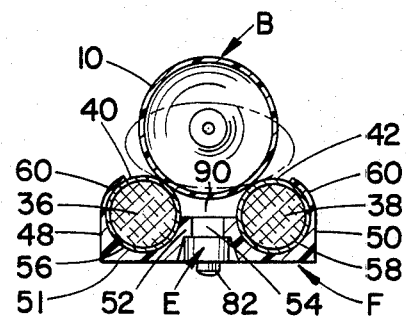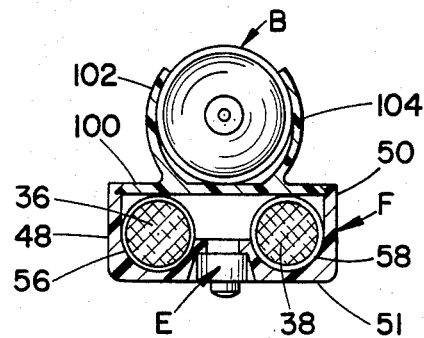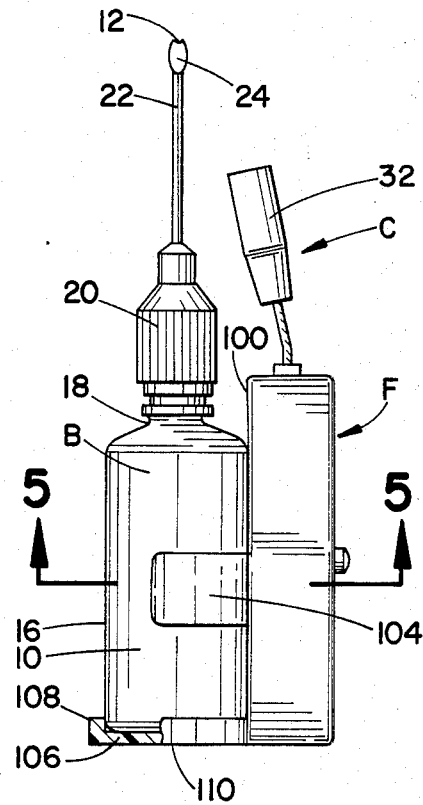

EYE DROPPER WITH LIGHT SOURCE

BACKGROUND

The present invention pertains to the art of liquid dispensers and, more particularly, to a device for illuminating the dispensing end of a droplet dispenser. The invention is particularly applicable for use with an eye dropper and will be described with particular reference thereto, although it will be appreciated that the invention has other and broader applications.

BACKGROUND OF THE INVENTION

Eye drop dispensers of a type comprised of a relatively small compressible plastic container and dispensing cap with a drop dispensing tip having an orifice or opening therein are generally well known. These dispensers come in numerous sizes and shapes, and are widely used for administering medicant drops to a patient's eye.

When using such dispensers, it is extremely important to accurately position the dispensing nozzle with respect to the eye, not only to avoid injuring the eye, which may be caused by accidental contact of the nozzle with the eye, but also to avoid waste or loss of the medicant. Most medicants for use in the eye are extremely expensive and a single drop can represent substantial expense. In addition, when using these dispensers, it is important to accurately determine the amounts of medicant dispensed, i.e. the number and size of the drops dispensed. Some eye medicants require exact doses, too little or too much may not provide the desired medical results.

Regardless of the manner in which a person tries to insert drops into an eye, it is difficult to clearly see or to focus on the dispensing tip and/or the surface of the eye when the dispenser and dispensing tip are so near the eye. A reason for this difficulty is that the dispensing tip and the area where the drops are to be dispensed are generally shadowed or obscured by the dispensing bottle and the user's own hand. The dispenser bottle and hand are generally so near the eye that they partially block any surrounding light, and cast shadows which darken the surface of the eye and the dispensing tip. Likewise, the very shape of the human face magnifies this problem. The human eye is basically recessed into sockets in the human skull, which sockets protect the eye, but also create a dim shaded cavity surrounding the eye. For these reasons, it is extremely difficult for the patient to focus on the dispensing tip and the surface of the eye when drops are to be dispensed. In addition, drops may be inserted in areas of dim lighting such as a doctor's waiting room or a patient's bedroom or hospital room. This problem is greatly exaggerated for people of advanced age or those with severe vision impairment. For these elderly or visually handicapped persons, it is extremely difficult to focus on objects which are not clearly illuminated.

Changes in the design of the dispensing cap or bottle can, to a certain extent, enable more accurate positioning of the dispensing tip with respect to the surface of the eye. For example, in my co-pending application Ser. No. 372,966, now U.S. Pat. No. 4,471,890, and Ser. No. 372,967, now abandoned, dispensing devices are disclosed which are easy to use, and which dispense small drops of liquid more accurately than conventional eye droppers. The disclosures of these applications are incorporated by reference herein. In addition, these dispensers may be used even while corrosive lens or eyeglasses are worn. Yet these dispensers do not overcome the problem of the dim or dark areas surrounding the eye, or improve the ability to clearly see and focus on the dispensing tip and orifice and/or surface of the eye. In fact, conventional eyeglasses increase this problem. Rims of such eyewear and the lens themselves diffuse existing light making it even more difficult to focus on specific objects. Thus, even though these dispensers enable better positioning of the dispenser tip and more exact dispensing of the liquid, if the tip itself and the surrounding area of the eye are not clearly visible, accurate positioning cannot be obtained, and the amount of medicant dispensed cannot be exactly determined.

The present invention contemplates a device for use with a medicant drop dispenser, which device overcomes the above-identified problems and others, by illuminating the area about the dispensing tip end of the dispenser, so as to enable a person to clearly see the dispenser tip, and to easily dispense medicant drops into a person's eye with greater accuracy, and which device is simple, economical and easy to use.

THE INVENTION

In accordance with the present invention, there is provided for use with a container for drops to be dispensed and a dispensing orifice spaced from the container, a light source capable of projecting a collimated beam of light, a battery support, and a switch device for controllably connecting the light source with a battery held by the battery support, wherein the battery support and the light source are positioned relative to the container such that the collimated beam from the light source projects along a predetermined path onto the dispensing orifice.

Further in accordance with the present invention, the battery support, a light source mount and a housing for the switch device comprise a body member, which member is adapted to receive and locate a medicant drop dispenser relative thereto such that the dispensing orifice of the dispenser may be held in a position which is a predetermined distance from the light source, and wherein the position of the dispensing orifice and the path of the beam are adjustable with respect to each other.

Still further in accordance with the present invention, a device of the foregoing character is provided wherein the switch device automatically actuates the light source whenever the device is in a drop dispensing orientation.

An object of the present invention is the provision of a device which enables a person using a medicant drop dispenser having a dispensing tip to position more accurately the dispensing tip with respect to the surface of the eye and to dispense the amounts of medicant more accurately.

Another object of the present invention is to provide a device of the foregoing character which device illuminates a zonal area adjacent the dispensing tip of a drop dispenser.

A still further object of the present invention is its provision of a device of the foregoing character which device may be used with most commonly available eye drop dispensers.

Another object of the present invention is to provide a device of the foregoing character which is light, compact and may be easily manipulated and used with one hand.

A still further object of the present invention is the provision of a device of the foregoing character which is simple, inexpensive, and easy to use.

The invention may take physical form in certain parts and arrangements of parts, preferred embodiments which will be described later in detail in this specification and illustrated in the accompanying drawings which form a part thereof and wherein:

FIG. 1 is a side elevational view of a device in accordance with the present invention illustrating application of the device with a drop dispenser incorporating the concept of my co-pending application Ser. No. 372,967;

FIG. 2 is a front elevational view of the device shown in FIG. 1;

FIG. 3 is a sectional view taken along line 3—3 in FIG. 1;

FIG. 4 is a side elevational view of an alternate embodiment in accordance with the present invention shown with a drop dispenser; and, FIG. 5 is a sectional view taken along line 5—5 in FIG. 4.

DETAILED DESCRIPTION OF THE PREFERRED EMBODIMENT

Referring now to the drawings wherein the showing is for the purpose of illustrating preferred embodiments of the invention only and not for the purpose of limiting same, the Figures show a device A for illuminating a zonal area adjacent a dispensing orifice associated with a drop dispenser. Briefly stated, device A includes a drop dispenser B having a container 10 for drops to be dispensed with a dispensing orifice 12 relative thereto, a light source C capable of projecting a collimated beam of light 14 along a predetermined path, a self-contained energy source D, and a switch device E controllably connecting the light source to the energy source. Means are provided to support light source C, energy source D, and switch E relative to container 10 such that beam 14 projects along the predetermined path onto dispensing orifice 12. The supporting means for light source C and energy source D could be integrally formed with container 10 to provide a single unit, as will be discussed in more detail later. However, the means for mounting or supporting light source C and energy source D is preferably provided in the form of an independent body member F, which member as an independent unit finds advantageous application with most commercially available medicant drop dispensers. Since drop dispenser B in and of itself forms no part of the present invention, it will not be described in great detail. Drop dispenser B is basically comprised of a compressible plastic container or vial 10, having an outer surface 16. Any plastic container or vial 10, such as commonly used in conjunction with eye drop dispensers, would include a reduced diameter neck portion 18 provided with external screw threads (not shown). The screw threads are adapted to matingly engage the internal threads on cap member 20 in a relatively conventional manner, to thereby attach the latter in place on container 10. The Figures show cap member 20 incorporating the concepts disclosed in my aforementioned co-pending application Ser. No. 372,967. Cap member 20 is provided with an elongated flexible dispensing tube 22 with a dispensing tip 24 of a resilient soft material at the end thereof, having a dispensing orifice or opening 12 therein.

As mentioned above, light source C projects a collimated beam of light 14 along a predetermined path and intersects with orifice 12, thereby illuminating the orifice and the area immediate thereto. Light may be projected from a light source to orifice 12 in several ways, such as with a mirror arrangement or by optical fibers; but in the preferred embodiment light source C is comprised of a miniature lamp or bulb 30 which produces a generally collimated beam of light 14. As will be described hereinafter, the direction or path of beam 14 is adjustable relative to orifice 12 and body member F. Bulb 30 is approximately ⅛ inch (3 millimeters) in diameter, and produces approximately 0.05 mean spherical candle power (0.6285 lumens) in a generally directional beam. The bulb is a product of General Electric Company and is from a G.E. grouping of bulbs designated T-1. It will be appreciated that the actual size and intensity of the bulb is not critical to the present invention. The bulb need only be small enough and bright enough to lend itself to suitable application with a device as described in this application. Lamp or bulb 30 is partially enclosed by a sleeve 32 which blocks or limits radiation of light from the sides of the bulb and as a result provides a more directional or collimated beam of light.

Power source D is comprised of two AA-sized dry cell batteries 36 and 38 having outer surfaces 40 and 42 respectively. As is appreciated, batteries come in numerous sizes and shapes. The present invention is not limited to any specific size or shape, any battery or batteries having sufficient power to illuminate bulb 30 may be used.

As set forth above, means for supporting light source C and energy source D relative to container 10 and orifice 12 is provided in the form of body member F. Body member F may be cut, molded or otherwise formed from several materials, but is preferably of molded plastic construction to provide a light-weight structure. Body member F is rectangular in shape, and comprised of pairs of opposed end walls 44, 46 and side walls 48, 50 integral with a back portion 51. Side walls 48 and 50 are parallel to each other and extend along the length of body member F. A rib or ridge 52 is centrally located between side walls 48 and 50 along back portion 51, and extends along the length of the body member. Ridge 52 has an opening 54 molded, formed or otherwise provided therein. Between ridge 52 and wall members 48 and 50, arcuate grooves or troughs 56 and 58 are provided respectively. Grooves 56 and 58 are adapted to receive batteries 36 and 38. Arcuate tabs 60 are provided on side wall members 48 and 50. Together grooves 56 and 58, and tabs 60 form a locking and holding arrangement as is conventionally known for receiving and holding batteries.

End walls 44 and 46 are each provided with a spring contact 62 and a solid contact 64 for engaging the poles of batteries 36 and 38. Contacts 62 and 64 on wall members 44 and 46 are positioned in a generally conventional manner and are aligned with the axes of batteries 36 and 38 to hold the batteries in engagement therewith. Contact posts 68 and 70 are provided on wall members 44 and extend therethrough in engagement with spring contact 62 and solid contact 64. Bulb 30 is connected to posts 68 and 70 by wire leads 76 and 78 respectively. Leads 76 and 78 are of such a diameter so as to rigidly hold bulb 30 in a fixed position, yet flexible enough so as to allow adjustment of bulb 30 and beam 14 with respect to body member F and orifice 12. Wire leads 76 and 78 may be secured to contact posts 68 and 70, and to the terminals of lamp 30 by conventional means, such as soldering. A switch device 80 is comprised of a momentary contact switch element and is provided between, and connected to, batteries 36 and 38 by lines 72 and 74. Switch element 80 is located within opening 54 in ridge 52 of body member F, such that only button 82 of switch 80 extends beyond the outer surface of body member F.

Importantly, body member F is adapted to receive and locate a dispenser relative thereto so as to position and maintain a positional relationship between the dispensing tip of the dispenser, and the path of the light beam 14. In the embodiment shown in FIGS. 1 through 3, dispenser B is preferably held against device F. Locating the dispenser is accomplished by the outer surfaces 40 and 42 of batteries 36 and 38. As best seen in FIG. 3, a channel-way 90 is provided between batteries 36 and 38 and ridge 52. The outer surface 16 of container 10 abuts or rests against battery surfaces 40 and 42. Whereas the batteries are parallel to each other, and engage container 10 along most of its length, container 10 rests snuggly in channel-way 90, and is held easily as shown in FIG. 1. Since container 10 is not fixedly secured by the device, the container may slide or be moved with respect to the batteries along the axes of the batteries. This movement in conjunction with the adjustability of lamp bulb 30 enables easy positioning of the dispensing orifice 12 with respect to beam 14. As will be appreciated, a device of such an arrangement is amendable for use with a wide variety of dispenser container shapes. For example, the cross-sectional view of a conventional oval-shaped container is shown in phantom in FIG. 3. The oval shape rests conveniently in channel way-90 and engages, and is supported by, the outer surfaces 40 and 42 of batteries 36 and 38.

FIGS. 4 and 5 illustrate an alternate embodiment of body member F in accordance with the present invention, wherein instead of a channel-way 90, structural members are provided on body member F for positioning dispenser 10 with respect thereto. Light source C, electrical energy source D and switch device E are all similar to those shown in the aforementioned embodiment illustrated in FIGS. 1-3. Body member F, however, is modified to totally enclose batteries 36 and 38. Body member F is similar to the body member previously described but has been adapted to accept a cover or lid 100 in a manner relatively conventional for such enclosures. Lid or cover 100 includes arcuate, resilient arm portions 102 and 104 which are spaced from one another and adapted to surround and grip a proportion of drop dispenser B. Cover 100 is also provided with a laterally extending member 106 having a flange 108 extending around the periphery thereof, and a bottom surface 110. Surface 110 is generally planar with the end surface of body member 10. As can be seen, resilient arm members 102 and 104 maintain container 10 of drop dispenser B in position relative to body member F. Member 106 also assists in positioning dispenser B, and further provides a flat surface 110 upon which dispenser B and device A may be set so as to place the combination in an upright position as best seen in FIG. 4.

In operation, the aforementioned embodiments may be used with most conventional drop dispensers. Preferably, the embodiments are used with a drop dispenser B according to my previously mentioned application Ser. No. 372,967. Dispenser B is positioned against body member F such that the dispensing tip intersects the path of light beam 14. Light source C may be adjusted to direct the beam of light relative to body member F and relative to the dispensing tip of the dispenser. The position of the dispenser along body member F and the direction of beam 14 may be adjusted until the tip end of the dispenser and the light beam intersect, which then provides an illuminated zonal area around the dispensing tip. The dispenser container can be easily held in position with one hand as shown in FIG. 1.

With the present invention, sufficient light is provided around the dispensing tip end of the dispenser to enable a patient, or even another person, to see more clearly and, therefore, position more accurately the dispensing tip with respect to the surface of the eye. Likewise, by providing an illuminated, clearly visible dispensing orifice, the number and size of the drops from the dispenser can be easily determined.

The foregoing specification described preferred embodiments of the present invention. It will be appreciated that modifications and alterations may be made to the various elements disclosed in the present invention without deviating therefrom. For example, in the preferred embodiment the power source consisted of AA-sized dry cell batteries arranged side-by-side. The power source, however, could be any battery of any shape having sufficient power to energize the light source. Preferably, the batteries or any other energy source are of a size which can be easily held by hand, and provide suitable energy.

The main purpose of the switching device is to prevent constant energization of the light source when the device is not in use. The switching device therefore may be one of the numerous types of electrical switches which are commercially available. In the preferred embodiment a momentary switch is disclosed, which switch must remain depressed to activate the light source. Any other type of switch element may be used so long as the switch is an appropriate size for use with the device. Recent developments of the present invention have shown that a mercury switch is particularly suitable for an embodiment such as shown in FIG. 4. With such arrangement dispenser B and body member F would be stored in an upright position wherein the switch would be deactivated, and would activate only when the dispenser was in a generally horizontal position.

As will be appreciated, the general shape of body member F may vary greatly, depending on a numerous modification and arrangement of the electrical power source and the switch device. Likewise, the shape of body member F would depend on whether dispenser B is to be held in place by the hand of a user, or is to be held by a portion of the member itself. It is only important that the dispenser be located and held in a stationary position relative to body member F and that the tip end of the dispenser will intersect the path of the light beam, or will intersect the path of the beam after adjusting the direction of the light source.

In addition to the finger or clamp arrangement shown in FIGS. 4 and 5, dispenser B may be held in position relative to body member F by other means such as adhesive tape, or Velcro-strap, or even a sleeve into which dispenser B may be inserted. In addition, it will also be appreciated that though the Figures illustrate a device separate from drop dispenser B, the dispenser bottle itself could be molded or otherwise fabricated to receive the other elements of the present invention, i.e. the lamp, siwtch and batteries so as to provide an integral unit having a beam of light intersecting the tip end of the dispenser. Other uses and additional modifications and alterations will occur to others upon their reading and understanding of this specification. It is intended that all such modifications and alterations be included insofar as they come within the scope of the invention as claimed or the equivalence thereof.

Having thus described the invention, it is claimed:

1. In combination, an eye drop dispenser including a compressible plastic container for the drops to be dispensed and an elongated, small diameter tubular dispensing member communicating with said container and having a dispensing orifice spaced therefrom, and a device for illuminating said dispensing orifice, said device comprising:
(a) a body member,
(b) a self-contained energy source carried by said body member,
(c) a light source mounted to said body member at a position located away from said dispensing orifice to provide an unobstructed area along a major portion of said tubular dispensing member, said light source being capable of projecting a collimated beam of light,
(d) a switch carried by said body member, said switch being operable to selectively connect said energy source to said light source, and
(e) aligned surfaces forming a channel-way receiving said container to provide a stable orientation of said container with respect to said device while permitting shifting movement therebetween in a direction generally aligned with said tubular dispensing member.

2. A combination as defined in claim 1, wherein, said container is hand-held in said channel-way such that said container is slidable along said channel-way to align said beam with said orifice.

3. A combination as defined in claim 1, wherein said switch is a mercury switch arranged on said body member so as to activate said light source when said device is in a drop dispensing orientation.

4. A combination as defined in claim 1, wherein said body member includes resilient arm portions extending therefrom, said arm portions providing said aligned surfaces and surrounding at least a portion of said container to secure said container to said body member while allowing movement therebetween.

5. A combination as defined in claim 1, wherein said light source is movably mounted to said body member.

* * * * *